(12) United States Patent
Hong et al.

(10) Patent No.: US 8,974,438 B2
(45) Date of Patent: Mar. 10, 2015

(54) COMPACT CATHETER ASSEMBLY

(71) Applicant: Compactcath, Inc., Palo Alto, CA (US)

(72) Inventors: Daniel Wei-Chen Hong, Cupertino, CA (US); Myung Sun Choi, Pittsburgh, PA (US); Katherine Muterspaugh Steele, Seattle, WA (US); David Philip Janka, San Francisco, CA (US); Sean Kshitij Mehra, Palo Alto, CA (US); Naama Stauber, San Francisco, CA (US)

(73) Assignee: Compactcath, Inc., Palo Alto, CA (US)

( * ) Notice: Subject to any disclaimer, the term of this patent is extended or adjusted under 35 U.S.C. 154(b) by 0 days.

(21) Appl. No.: 14/043,750

(22) Filed: Oct. 1, 2013

(65) Prior Publication Data

US 2014/0031799 A1    Jan. 30, 2014

Related U.S. Application Data

(63) Continuation of application No. 13/485,750, filed on May 31, 2012, now Pat. No. 8,556,884.

(60) Provisional application No. 61/491,492, filed on May 31, 2011.

(51) Int. Cl.
*A61M 25/00* (2006.01)
*A61M 25/01* (2006.01)
(Continued)

(52) U.S. Cl.
CPC ............ *A61M 25/0097* (2013.01); *B65H 75/00* (2013.01); *B65H 49/205* (2013.01);
(Continued)

(58) Field of Classification Search
CPC ........ B65H 49/00; B65H 49/18; B65H 49/20; B65H 49/205; B65H 49/24; B65H 49/32; B65H 49/322; B65H 49/324; B65H 54/00; B65H 54/02; B65H 54/40; B65H 54/42; B65H 54/44; B65H 54/46; B65H 75/00; B65H 54/585; B65H 75/02; B65H 75/05; B65H 54/106; B65H 54/12; B65H 54/22; B65H 54/28; B65H 54/10; H02G 11/02; H02G 11/00; A61M 25/0017; A61M 25/002; A61M 25/0097; A61M 25/0111; A61M 25/0113; A61M 2039/087

See application file for complete search history.

(56) References Cited

U.S. PATENT DOCUMENTS 2,711,734 A * 6/1955 Moe .............................. 604/171
3,683,928 A    8/1972 Kuntz
(Continued)

FOREIGN PATENT DOCUMENTS

DE    20009506 U1    10/2001
EP    0820781 A1    1/1998
(Continued)

OTHER PUBLICATIONS

Partial International Search Report for PCT/US2012/040277, Mailed Jul. 20, 2012. (2 pages).

*Primary Examiner* — Adam Marcetich
(74) *Attorney, Agent, or Firm* — Dorsey & Whitney LLP

(57) ABSTRACT

Packaging including a coiled and optionally prelubricated catheter, its distal end insertable into the urethra, a slidable hygienic sheath, a proximal catheter end for voiding urine from the distal end through the assembly to the proximal end. Mutually rotatable elements providing for withdrawal of the catheter from its coiled state to an extended state, and retraction of the catheter back to its coiled state. Methods of extending the catheter, inserting it into the urethra, and voiding urine through the catheter, without requiring complete removal from the catheter packaging. A kit including automatic extrusion of the catheter's distal end upon package opening, and a water pouch for hydrophilic lubrication, and sanitary wipes for reducing the likelihood of infection. A catheter within a flexible and optionally coiled tube, a slidable hygienic sheath covering a catheter's distal end that can move along the length of the catheter during insertion.

8 Claims, 7 Drawing Sheets

(51) Int. Cl.
| | |
|---|---|
| *B65H 75/00* | (2006.01) |
| *B65H 49/20* | (2006.01) |
| *B65H 54/40* | (2006.01) |
| *A61M 39/08* | (2006.01) |
| *B65H 54/44* | (2006.01) |
| *B65H 54/02* | (2006.01) |
| *B65H 54/58* | (2006.01) |
| *B65H 54/46* | (2006.01) |
| *B65H 75/02* | (2006.01) |

(52) U.S. Cl.
CPC ......... *B65H 54/40* (2013.01); *A61M 2039/087* (2013.01); *B65H 54/44* (2013.01); *B65H 54/02* (2013.01); *B65H 54/585* (2013.01); *B65H 54/46* (2013.01); *B65H 49/20* (2013.01); *B65H 75/02* (2013.01); *A61M 25/0017* (2013.01); *A61M 25/002* (2013.01); *A61M 25/0111* (2013.01); *A61M 25/0113* (2013.01)
USPC ............ 604/544; 604/540; 604/317; 604/327

(56) References Cited

U.S. PATENT DOCUMENTS

| | | | |
|---|---|---|---|
| 3,806,992 A * | 4/1974 | Reimer | ............... 242/378.3 |
| 4,160,451 A | 7/1979 | Chittenden | |
| 4,244,536 A | 1/1981 | Harrill | |
| 4,311,050 A | 1/1982 | Bessman | |
| 4,384,688 A | 5/1983 | Smith | |
| 4,467,979 A | 8/1984 | Koehler | |
| 4,656,320 A | 4/1987 | Maddock | |
| 4,811,847 A | 3/1989 | Reif et al. | |
| 4,835,003 A | 5/1989 | Becker et al. | |
| 4,903,826 A | 2/1990 | Pearce | |
| 4,921,096 A | 5/1990 | McFarlane | |
| 5,103,977 A | 4/1992 | Douglas | |
| 5,125,416 A | 6/1992 | Phillips | |
| 5,344,011 A | 9/1994 | DiBernardo et al. | |
| 5,372,254 A | 12/1994 | Gross | |
| 5,392,918 A | 2/1995 | Harrison | |
| 5,421,457 A * | 6/1995 | Listenberger | ............... 206/388 |
| 5,730,150 A | 3/1998 | Peppel et al. | |
| 5,738,213 A | 4/1998 | Whiting et al. | |
| 5,769,222 A | 6/1998 | Banerian | |
| 5,915,640 A | 6/1999 | Wagter et al. | |
| 5,915,641 A | 6/1999 | Barberg | |
| 6,056,226 A | 5/2000 | Green | |
| 6,086,008 A | 7/2000 | Gray et al. | |
| 6,375,006 B1 * | 4/2002 | Samuels | ............... 206/364 |
| 6,719,135 B2 | 4/2004 | Armijo | |
| 6,902,057 B2 | 6/2005 | Duffy | |
| 7,191,900 B2 | 3/2007 | Opie et al. | |
| 7,234,597 B2 | 6/2007 | Rowe et al. | |
| 7,549,270 B2 | 6/2009 | Rowe et al. | |
| 7,640,714 B2 | 1/2010 | Waller et al. | |
| 7,682,353 B2 | 3/2010 | Tanghoj et al. | |
| 7,766,162 B2 | 8/2010 | Maki et al. | |
| 7,789,873 B2 | 9/2010 | Kubalak et al. | |
| 7,867,220 B2 | 1/2011 | Tanghoj | |
| 7,922,712 B2 | 4/2011 | Tanghoj et al. | |
| 8,556,884 B2 | 10/2013 | Hong et al. | |
| 8,708,999 B2 * | 4/2014 | Hong et al. | ............... 604/544 |
| 2002/0145073 A1 | 10/2002 | Swanson et al. | |
| 2003/0015617 A1 | 1/2003 | Chuang | |
| 2004/0055919 A1 | 3/2004 | Rowe et al. | |
| 2005/0109648 A1 | 5/2005 | Kerzman et al. | |
| 2006/0016480 A1 | 1/2006 | Cheng | |
| 2006/0048819 A1 | 3/2006 | Dean | |
| 2006/0058777 A1 | 3/2006 | Nielsen | |
| 2006/0142737 A1 | 6/2006 | Tanghoj | |
| 2006/0186256 A1 | 8/2006 | Mogensen et al. | |
| 2006/0260968 A1 | 11/2006 | Mayda et al. | |
| 2006/0271019 A1 * | 11/2006 | Stoller et al. | ............... 604/544 |
| 2008/0017745 A1 | 1/2008 | Laga | |
| 2009/0054876 A1 | 2/2009 | Borodulin et al. | |
| 2009/0071851 A1 | 3/2009 | Maki et al. | |
| 2009/0137985 A1 | 5/2009 | Tanghoej et al. | |
| 2009/0149837 A1 | 6/2009 | Tanghoj et al. | |
| 2009/0200187 A1 | 8/2009 | Nestenborg et al. | |
| 2009/0204106 A1 | 8/2009 | Golden | |
| 2009/0208368 A1 | 8/2009 | Waldrep et al. | |
| 2009/0277988 A1 | 11/2009 | Hernik | |
| 2010/0087801 A1 | 4/2010 | Torstensen et al. | |
| 2010/0130923 A1 | 5/2010 | Cleary et al. | |

FOREIGN PATENT DOCUMENTS

| | | |
|---|---|---|
| EP | 1023882 A1 | 8/2000 |
| WO | 9856687 A1 | 12/1998 |
| WO | 0178824 A1 | 10/2001 |
| WO | 2004022433 A2 | 3/2004 |
| WO | 2004054653 A1 | 7/2004 |
| WO | 2007081264 A1 | 7/2007 |
| WO | 2008089770 A1 | 7/2008 |
| WO | WO2012-166967 | 12/2012 |

* cited by examiner

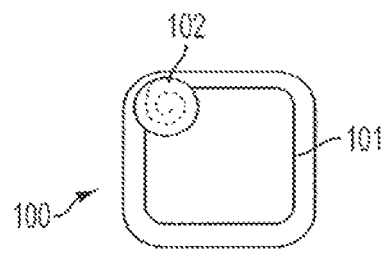
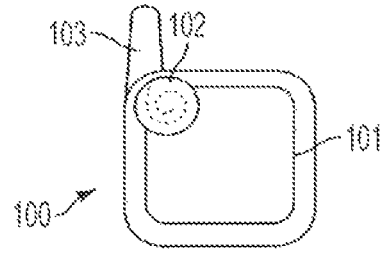
FIG. 1A    FIG. 1B
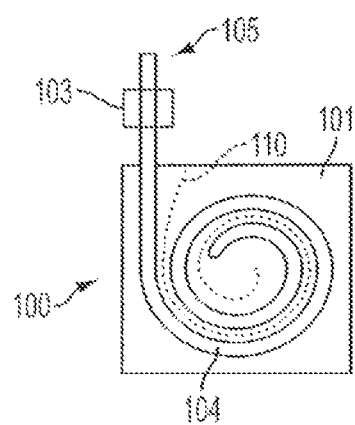
FIG. 1C

COMPACT CATHETER ASSEMBLY

CROSS-REFERENCE TO RELATED APPLICATIONS

This application is a continuation of pending U.S. patent application Ser. No. 13/485,750, filed May 31, 2012, entitled "Compact Catheter Assembly," which claims priority to U.S. Provisional Patent Application Ser. No. 61/491,492, filed May 31, 2011. The above-referenced applications are hereby incorporated by reference as if fully set forth herein.

BACKGROUND

1. Field of the Disclosure

This application generally relates to urinary catheters, assemblies including urinary catheters, and medical uses thereof.

2. Background of the Disclosure

Some patients require urinary catheters to effectively and hygienically void their bladder, such as those patients who suffer from urinary incontinence or other medical disorders.

Urinary catheters are inserted into the bladder through the urethra in order to open the urinary sphincter and drain urine into an appropriate receptacle. A typical urinary catheter patient might void their bladder every two to four hours. In developed countries, urinary catheters are disposable (that is, they are not reused), with the effect of requiring the use of multiple catheters per day.

It sometimes occurs that urinary catheters for patient use are insufficiently compact, or otherwise involve relatively bulky equipment. For example, in current use, many catheters are packaged in an elongated form, with the effect that they are cumbersome for both storage and transport. This can have the effect that the urinary catheter, or its presence on the patient, is readily apparent, or is not easily conveyed by the patient or in the patient's clothing when in use, or is not easily concealed or otherwise attached to the patient's clothing when in use.

Similarly, it sometimes occurs that using a urinary catheter has the substantial possibility of social embarrassment for the patient due to the possibility of the catheter, or any associated medical equipment, or the fact of the patient's need for the urinary catheter, becoming observed in a social setting. This can also occur due to the urinary catheter, or its presence on the patient, becoming apparent, or not being well concealed by the patient's clothing. More recently, smaller and more discreet catheters have been developed, such as the "Speedi-Cath™ Compact" catheter by Coloplast, Inc., currently available for female users in the United States, and available for male and female users in Europe.

It sometimes occurs that it is difficult to handle lubricated catheters, as they are often designed to be slippery, so as to facilitate easy insertion into the urethra. For example, in current use, many catheters are either pre-lubricated with a water activated coating, or are designed to be lubricated with a gel after opening, in either case in order to make it easier for the urinary catheter to be inserted into the urethra. Moreover, these lubricating mechanisms can be inconvenient, as users must either deal with packaging fluid, or carry around a lubricant along with the urinary catheter.

It also sometimes occurs that using a urinary catheter can be unhygienic due to the possibility of touching the catheter with an unsanitary object, such as either the patient's hand, or a portion of the patient's body other than for insertion into the urethra. This can have more than one untoward effect. A first effect can be that use of an unhygienic urinary catheter might lead to a urinary tract infection, or other untoward medical condition. For example, when handling the catheter directly, users must generally ensure that their hands and the opening of the urethra are clean, in order to avoid contaminating the catheter and risking a urinary tract infection. A second effect can be that the urinary catheter must be disposed of after use, and replaced with another such catheter, with the concomitant difficulty of needing additional urinary catheters, as well as some form of storage for used catheters.

It also sometimes occurs that patients using a urinary catheter are reluctant to detach the catheter from its packaging for voiding their urine. For example, in current use, urinary catheters can be conspicuous and difficult to use, with the effect that self-conscious patients might be inclined to refrain from using them sufficiently often, particularly in certain social settings, with the concomitant possibility of bladder problems, kidney problems, or other medical conditions.

BRIEF SUMMARY OF THE DISCLOSURE

This application provides techniques, including devices, assemblies, and methods, which include compact packaging systems for urinary catheters, and use thereof.

In one embodiment, techniques include devices and assemblies, such as urinary catheters capable of compact storage in a coiled, helical, or related shape, which can be drawn out for emplacement in the male or female urethra in an hygienic manner, and which can be used in their compact stored shape to void the bladder both hygienically and discreetly. For example, a compact system can include packaging for a urinary catheter which is small enough to fit in the palm of the hand.

In one embodiment, techniques include devices and assemblies, such as urinary catheters packaged with an enclosed hygienic sheath, such as one covering at least a portion of the catheter tip, with the effect that the urinary catheter patient can remove the urinary catheter from its package without substantial risk of unsanitary handling of the urinary catheter (as there is no substantial need for the user to directly touch the catheter), and that the patient can move the enclosed hygienic sheath along the catheter only when the catheter tip needs to be exposed for insertion into the urethra, and with the effect that it is relatively easier for the user to handle a lubricated catheter.

In one embodiment, techniques include devices and assemblies, such as urinary catheters capable of fitting within a flexible tubing or related container, which can be maintained within compact storage in an hygienic manner, and which can be used in their compact stored shape to void the bladder both hygienically and discreetly. For a first example, such devices and assemblies can include the described hygienic sheath, which can be initially part of the packaging, and which can be detached from the catheter at least in part, and which can be moved with respect to a distal end of the catheter so that the urinary catheter patient can use the catheter without having to touch it directly.

In one embodiment, techniques include devices and assemblies, such as urinary catheters positioned within a flexible tubing or related container, and lubricated, with the effect that the catheter can be moved with respect to the flexible tubing. For a first example, such devices and assemblies can include a hydrophilic lubricant, which can be maintained on the catheter in packaging and which can be activated at a time before or when the packaging is opened.

In one embodiment, techniques include devices and assemblies, and methods of operating those devices and assemblies, which provide for retraction of the urinary catheter into the package in a relatively simple and easy manner. For example, such devices and assemblies can include a rewinding feature, by which a urinary catheter patient can retract the urinary catheter back into the package and reassemble the urinary catheter back into its original coiled form. This has a first effect that the urinary catheter can be relatively easily repackaged for disposal after use. This has the effect that the urinary catheter can be relatively easily repackaged without substantial risk of contamination from a used catheter.

In one embodiment, techniques include methods, such as maintaining urinary catheters in a coiled, helical, or related compact shape within an assembly capable of allowing such urinary catheters for being withdrawn from the assembly hygienically and discreetly. For example, such methods can include re-emplacing such urinary catheters in that coiled, helical, or related compact shape within such assemblies. In alternative embodiments, such methods can include disposing such urinary catheters in that coiled shape within assemblies which are designed to maintain that coiled shape, such as a container including a relatively rigid spiral inner wall into which the catheter is fit.

In one embodiment, techniques include a relatively compact system that includes handles for opening a package including a urinary catheter, and sanitary wipes attached or incorporated into the packaging, with the effect of reducing the likelihood of a urinary tract infection. For example, a package of sanitary wipes can be incorporated into the packaging, or otherwise attached, (A) on a back of the compact catheter assembly, (B) in or near a central hole defined by the compact catheter assembly, or (C) at another location convenient for use by the urinary catheter patient.

In one embodiment, techniques include a relatively compact system that includes a package including a urinary catheter, and disposed for relatively easy application, a lubricant attached or incorporated into the packaging, with the effect of reducing the difficulty of lubricating and emplacing the catheter. For a first example, a relatively small container of water can be disposed so that when pressure is applied, that water is applied to a hydrophilic substance to provide a lubricant. For a second example, the catheter can be pre-lubricated, with either a hydrophilic or other lubricant.

As described herein, techniques include a relatively compact system which provides urinary catheter patients with a system that is substantially more amenable to social settings outside of the hospital. Moreover, as described herein, techniques include a relatively compact system which provides benefits to medical personnel by reducing storage space requirements, increasing likelihood of hygienic use, and reducing or preventing medical noncompliance or hygiene-related medical complications. Moreover, as described herein, techniques include a relatively compact system which provides urinary catheter patients with the possibility of conveying multiple urinary catheters without the inconvenience of relative bulkiness, or the social risk of the urinary catheter becoming socially indiscreet due to its packaging.

While multiple embodiments are disclosed, including variations thereof, still other embodiments of the present disclosure will become apparent to those skilled in the art from the following detailed description, which shows and describes illustrative embodiments of the disclosure. As will be realized, the disclosure is capable of modifications in various obvious aspects, all without departing from the spirit and scope of the present disclosure. Accordingly, the drawings and detailed description are to be regarded as illustrative in nature and not restrictive.

BRIEF DESCRIPTION OF THE FIGURES

While the specification concludes with claims particularly pointing out and distinctly claiming the subject matter that is regarded as forming the present disclosure, it is believed that the disclosure will be better understood from the following description taken in conjunction with the accompanying Figures, in which:

FIG. 1A shows a conceptual drawing of a sealed package capable of holding a compact catheter assembly.

FIG. 1B shows a conceptual drawing of an opened package with a hygienic sheath.

FIG. 1C shows a conceptual drawing of an opened package with a portion of a catheter.

FIG. 1C shows a conceptual drawing of an opened package with a portion of a catheter.

DETAILED DESCRIPTION

Sealed Package

Figure 2A:
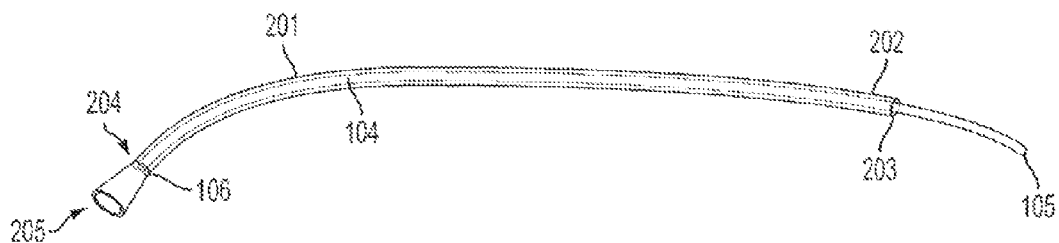
FIG. 2A shows a conceptual drawing of a catheter enclosed in an uncoiled flexible tubing.

FIGS. 1A-1C show conceptual drawings of a sealed package capable of holding a compact catheter assembly.

FIG. 1A shows a conceptual drawing of a closed package. FIG. 1B shows a conceptual drawing of an opened package with an hygienic sheath. FIG. 1C shows a conceptual drawing of an opened package with an extruded portion of a catheter.

Opening the Package.

As shown in FIG. 1A, a package 100 includes a sealed enclosure 101, optionally including a breakable, separable, or tearable corner which allows a user to more easily open the package 100 at a designated location.

In one embodiment, the enclosure 101 can be made of foil, glassine, plastic, or some other substance, such as a substance which is relatively opaque (so that urinary patients can be discreet about their use of a urinary catheter), which is at least moderately resistant to breakage or tearing (so that the content of the package 100 remains sterile), and which is relatively susceptible to sterilization (so that the package 100 can be made sterile when constructed).

In one embodiment, a corner where the patch 102 is located is made relatively more susceptible to breakage or tearing than the rest of the enclosure 101, allowing the manufacturer to more easily direct medical personnel where to best open the enclosure 101. In alternative embodiments, the patch 102 is optional. For example, in one example, the corner where the patch 102 is located might be made of paper, such as paper which is glued to the enclosure 101.

While the enclosure 101 is primarily described herein as made of a relatively flexible substance, in the context of the invention, there is no particular requirement for any such limitation. For example, the enclosure 101 may be made of a rigid material, such as a hard plastic, and the patch 102 may be disposed at a specific location intended for exit of the catheter from the package 100.

In such embodiments in which the enclosure 101 may contain a spiral wall made of a rigid material, such as a hard plastic, the catheter can be maintained within the enclosure 101 in a coil or spiral, such as by being disposed within a spiral inner guide-way, such as might be made by a spiral inner wall. In such embodiments, the catheter can still be withdrawn from the package 100, such as by providing a path using the spiral inner wall along which the catheter may be withdrawn from the package 100.

While the package 100 and the enclosure 101 are primarily described herein as being disposed for opening by the urinary catheter patient and withdrawal of the catheter from the package 100 upon opening, in the context of the invention, there is no particular requirement for any such limitation. For example, the package 100 and the enclosure 101 may be disposed in such manner that opening the package 100 causes or prompts an automatic extrusion of a portion the catheter, such as might be caused or prompted by compression or spring-loading of that portion of the catheter.

Hygienic Sheath.

As shown in FIG. 1B, in one embodiment, the package 100 includes a compact catheter assembly (not shown in this figure), optionally including a hygienic sheath 103, the latter being disposed to cover a distal end 105 of a catheter (not shown in FIG. 1B), the catheter being suitable for insertion in a male or female urethra. In one embodiment, the hygienic sheath 103 can include a first portion which is located at the catheter's distal end and which can be removed, and can include a second portion (not shown in this figure) which can be slidably moved along the catheter, so that the urinary catheter patient can handle the catheter without having to touch the catheter directly.

As described herein, the catheter can be manufactured in one or more sizes, such as relatively distinct lengths or widths. For example, the catheter can be manufactured in a relatively longer or shorter format, for male or female use respectively, or can be manufactured in a relatively narrower or wider format, for pediatric or adult use respectively.

In one embodiment, the hygienic sheath 103 might be made of a relatively flexible material, such as silicone, polyvinyl chloride, or another plastic material. However, in the context of the invention, there is no particular requirement for any such limitation. For example, the hygienic sheath 103 might be made of a form of latex or a latex-free equivalent substance.

As shown in FIG. 1B, the hygienic sheath 103 can be disposed so that it can be handled without exposure of the catheter 104 itself, with the effect that the catheter 104 itself can be maintained sterile even while the catheter 104 is being withdrawn from the package 100. As shown in FIG. 1C, the hygienic sheath 103 can be disposed so that the catheter 104 can include a distal end 105 which is extruded from the hygienic sheath 103 (with the hygienic sheath 103 being disposed to slide along the catheter 104), with the effect that the catheter's distal end 105 can be inserted into the urethra (not shown) while only the hygienic sheath 103 is handled by the patient (or alternatively, medical personnel), with the effect of maintaining the catheter's distal end 105 substantially sterile until it is actually inserted into the urethra.

In one embodiment, the catheter 104 might be made of a relatively flexible material, such as silicone, polyvinyl chloride, or another plastic material. However, in the context of the invention, there is no particular requirement for any such limitation. For example, the catheter 104 might be made of a form of latex or a latex-free equivalent substance.

As described below, in one embodiment, the catheter 104 can be enclosed in the package 100 in a substantially coiled form, with the effect that a relatively elongated catheter 104 can be enclosed within a relatively small package 100. For example, as described in further detail below, the catheter 104 can be enclosed in the package 100 in a coiled form substantially capable of being uncoiled for extension and re-coiled for reinsertion into the package 100.

In one embodiment, the catheter 104, when in the package 100, can be enclosed in a pre-lubricated form, such as by enclosing a lubricant within the package 100 in which the catheter 104 is immersed, or otherwise disposed for lubrication of the catheter 104, such as providing a hydrophilic substance which lubricates the catheter upon application of water. As described below, as the catheter 104 is removed from the package 100, it retains its pre-lubricated form, with the effect that the urinary catheter patient need not expend significant additional effort in either (A) lubricating a catheter 104, or (B) working with an otherwise slippery catheter 104 due to use of the hygienic sheath.

In one embodiment, the catheter 104, when in the package 100, can be maintained in a non-lubricated state, and lubricated by the urinary catheter patient before opening or during opening of the package 100. For example, the catheter 104 can be maintained coated with a hydrophilic lubricant, and coupled to a pouch including water. The patient would be able to press or squeeze the pouch to deliver water to the hydrophilic lubricant, with the effect of lubricating the catheter 104, or the package 100 could be made so that water can be delivered to the hydrophilic lubricant after opening the packaging, or with an alternative water source, or the package 100 can include a hydrophilic lubricant and a water source, or another lubricant.

In embodiments in which the catheter 104 is enclosed in a pre-lubricated form when in the package 100, the package 100 (or the enclosure 101) can include one or more drainage elements, such as gauze or holes, with the effect that the urinary catheter patient can remove any extra lubrication remaining in the package 100 (or the enclosure 101), or any extra water beyond that used to activate the hydrophilic lubricant, so that the urinary catheter patient can be assured that the package 100 will not leak additional lubrication, or additional water, onto unintended locations once the catheter 104 has been removed from the package 100 (whether or not yet inserted into the urethra).

The catheter 104 also includes a proximal end 106 (not shown in this figure). As described, in one embodiment, the proximal end 106 can be used by the urinary catheter patient for voiding urine into an appropriate receptacle, such as a public toilet, without the additional necessity for detaching the catheter 104 from a urinary receptacle, such as a urinary receiving bag or other medical equipment.

In one embodiment, the package 100 can optionally include one or more sanitary wipes 107 (not shown in this figure) or other similarly suited material, with the effect that medical personnel can maintain the catheter 104, the catheter's distal end 105, or the catheter's proximal end 106, substantially sterile even in the event of a mishap, or alternatively, to be used to sterilize the patient's hand before use. As described above, for example, the package of sanitary wipes 107 can be incorporated into the package 100, or otherwise attached in package 100, (A) on a back of the compact catheter assembly, (B) in or near a central hole defined by the compact catheter assembly, (C) attached to a coiled flexible tube, as described below, or (D) at another location convenient for use by the urinary catheter patient.

Spiral Internal Structure.

As shown in FIG. 1C, in alternative embodiments, a spiral internal structure 110 (shown as dotted lines), such as a vertical wall, can be disposed to guide the catheter 104 into a spiral shape, with the effect that a portion of the catheter 104 can be maintained in the enclosure 101 in a spiral form while the rest of the catheter 104 remains in the enclosure 101.

Flexible Enclosure

Figure 2B:
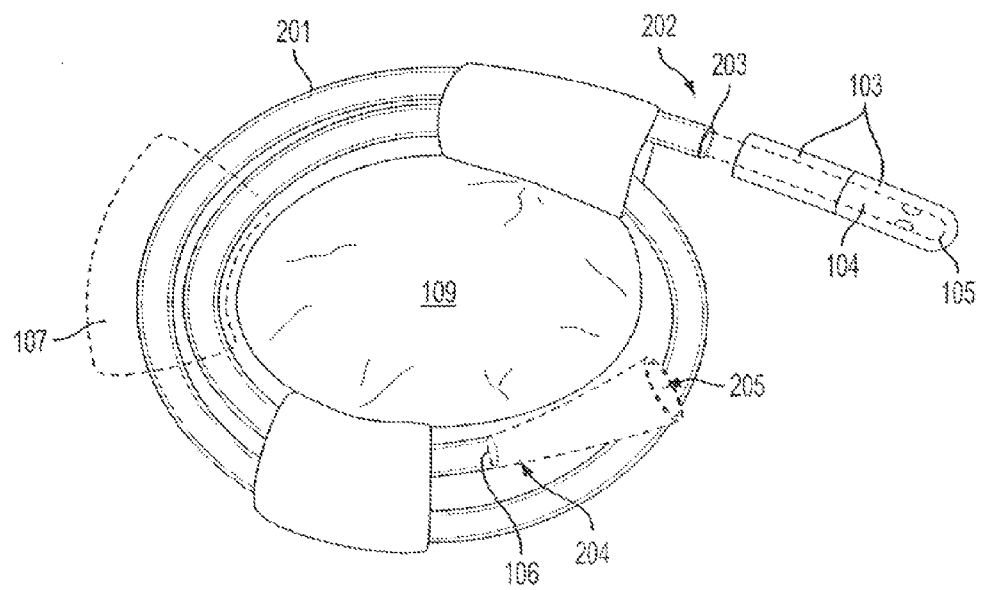
FIG. 2B shows a conceptual drawing of a catheter enclosed in a coiled flexible tubin.

FIGS. 2A and 2B show conceptual drawings of a catheter enclosed in a flexible tubing.

FIG. 2A, show a catheter enclosed in an uncoiled flexible tubing, and a FIG. 2B shows a catheter enclosed in a coiled flexible tubing.

As shown in the panel FIG. 2A and in FIG. 2B, a flexible tubing 201 encloses the catheter 104, with the effect that the catheter 104 is made relatively resilient to breakage or other damage, and with the effect that the catheter 104 can be bent or flexed in response to bending or flexing of the flexible tubing 201.

In one embodiment, the flexible tubing 201 might be made of a relatively flexible material, such as silicone, polyvinyl chloride, or another plastic material. However, in the context of the invention, there is no particular requirement for any such limitation. For example, the flexible tubing 201 might be made of a form of latex or a latex-free equivalent substance.

In one embodiment, the flexible tubing 201 includes a distal tubing end 202, defining a distal tubing hole 203. In one example, the catheter's distal end 105 can be pushed through the distal tubing hole 203, with the effect that the catheter's distal end 105 can be directly inserted into the urethra.

As described above, in one embodiment, the hygienic sheath 103 can include a first portion (shown as "removable end") which is located at the catheter distal end 105 and which can be removed, and can include a second portion (shown as "slidable portion") which can be slidably moved along the catheter. In such embodiments, the hygienic sheath 103 can be disposed so as to be separable from the distal tubing end 202.

In one embodiment, the flexible tubing 201 includes a proximal tubing end 204, defining a proximal tubing hole 205. In one embodiment, the proximal tubing hole 205 can be relatively wider than the main portion of the flexible tubing 201, with the effect that the proximal tubing hole 205 is relatively well suited for coupling to a receptacle (not shown in this figure) for urine to be voided.

Similar to the distal tubing end 202, in one embodiment, the proximal tubing end 204 can have a secondary sheath (not shown) which can be removed from the proximal tubing end 204, allowing exit of fluids such as urine from the proximal tubing hole 205. Having both the distal tubing end 202 and the proximal tubing end 204 covered has the effect that the inside of the flexible tubing 201 is sealed against air and any consequent contact with infectious elements.

In one embodiment, as described herein, urine is coupled from the urethra, through the catheter's distal end 105 and the distal tubing hole 203, through the main portion of the catheter 104, to the catheter's proximal end 106 and the proximal tubing hole 205, to one or more receptacles. For a first example, the receptacles can include a urine bag or other sanitary holding element. For a second example, the receptacles can include a flush toilet or other suitable sanitary element for removing urine.

As shown in FIG. 2B, the flexible tubing 201 can be disposed in a coiled or helical shape, with the effect that it takes relatively little space. For example, the flexible tubing 201, in its coiled or helical shape, can be fit into the package 100, which might look much like a package including a condom, with the effect that the presence of the catheter 104 with the urinary catheter patient can be made relatively convenient and discreet.

The hygienic sheath 103 can be disposed in two parts: a first portion which covers the catheter distal end 105, and which can be discarded, and a second portion which can be slidably moved along the catheter 104, such as after the catheter 104 has been lubricated, and which can be used by the urinary catheter patient to hold the catheter 104 without directly touching it.

In one embodiment, the coiled flexible tubing 201 can have one or more sanitary wipes 107 coupled thereto, with the effect that the sanitary wipes 107 are conveniently available to the urinary catheter patient when using the catheter 104.

In one embodiment, the coiled flexible tubing 201 can have a water pouch 109 or a pouch including a lubricant coupled thereto, and disposed so that when the urinary catheter patient presses or squeezes the water pouch 109, water is pressed or squeezed out of the water pouch 109 and into the flexible tubing 201 and onto the catheter 104. The water pouch 109 can be disposed in a position so that water is pressed or squeezed out even when the water pouch 109 is inside an unopened package 100. This has the effect that the patient can lubricate the catheter 104 relatively easily, even when the catheter 104 is still inside an unopened package 100, with the effect that the patient can have the catheter 104 ready and prepared for convenient and discreet use.

Construction of Tubing.

In one embodiment, the catheter 104 is manufactured within the flexible tubing 201 using a sequence of steps:

In a first step, the catheter 104 can be placed within the flexible tubing 201.

In a second step, the catheter 104 inside the flexible tubing 201 can be turned into a flexible spiral structure, and fixed, such as with heat or solvent.

In a third step, the catheter 104 inside the flexible tubing 201 can be placed into a condom-like enclosure 101.

In a fourth step, a distal end of the flexible tubing 201 can be detached, with the effect that the detached portion can serve as a sliding sheath for the catheter 104.

In a fifth step, one or more central portions of the flexible tubing 201 can be coupled to a water pouch, with the effect that the water pouch can pump (or exude) water into the flexible tubing 201 before use of the catheter 104. This has the effect that a hydrophilic coating of the catheter 104 can be activated before use of the catheter 104.

In a sixth step, the catheter 104 can be deployed from within the flexible tubing 201 for use.

In alternative embodiments, if the catheter 104 is maintained within the flexible tubing 201 during use of the catheter 104, one or more central portions thereof can serve as outlets for fluid entering the catheter 104.

Catheter Assembly

FIGS. 3A-3E show conceptual drawings of a catheter assembly, including a catheter maintained in a compact form factor.

Figure 3A:
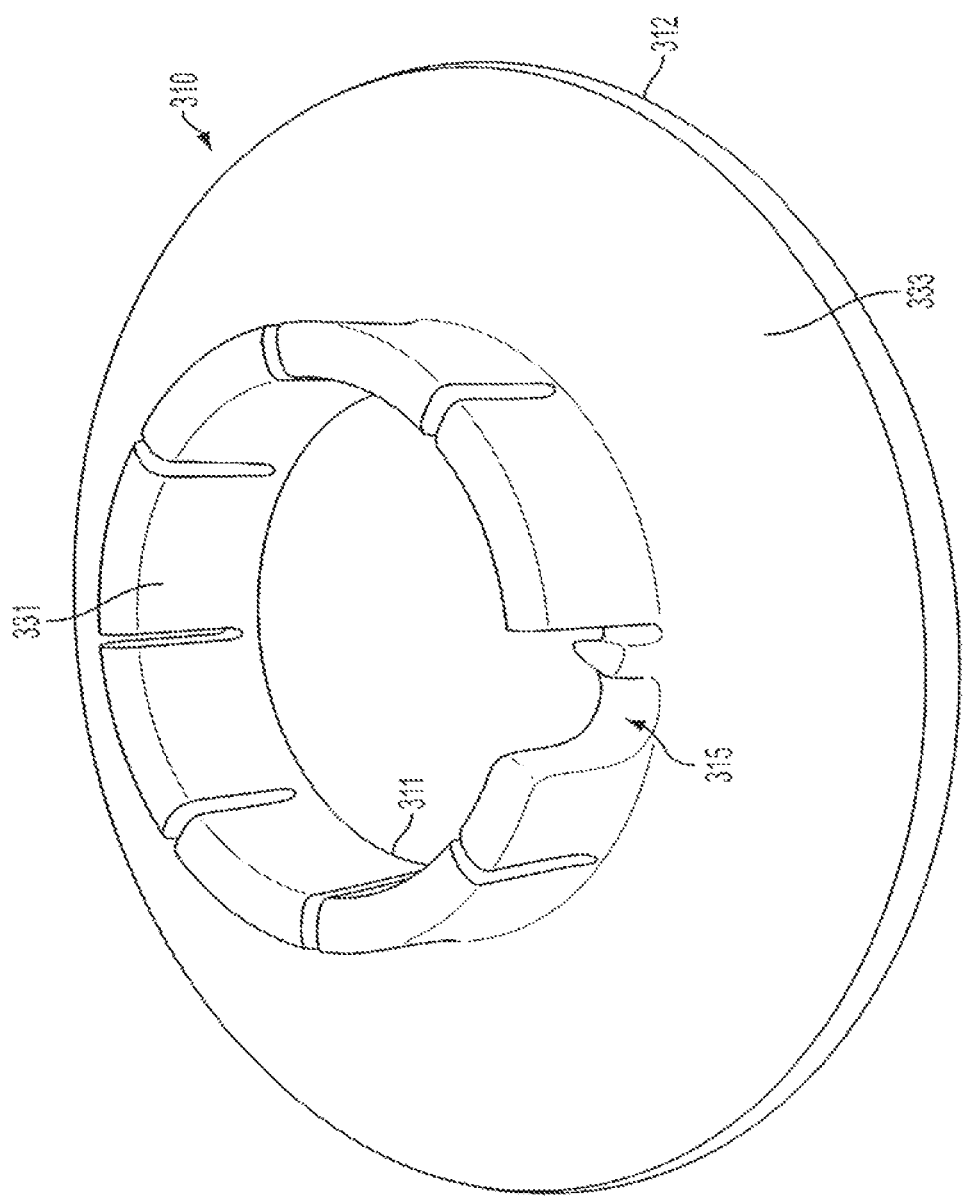
FIG. 3A shows a conceptual drawing of a bottom element of a catheter assembly.
Figure 3B:
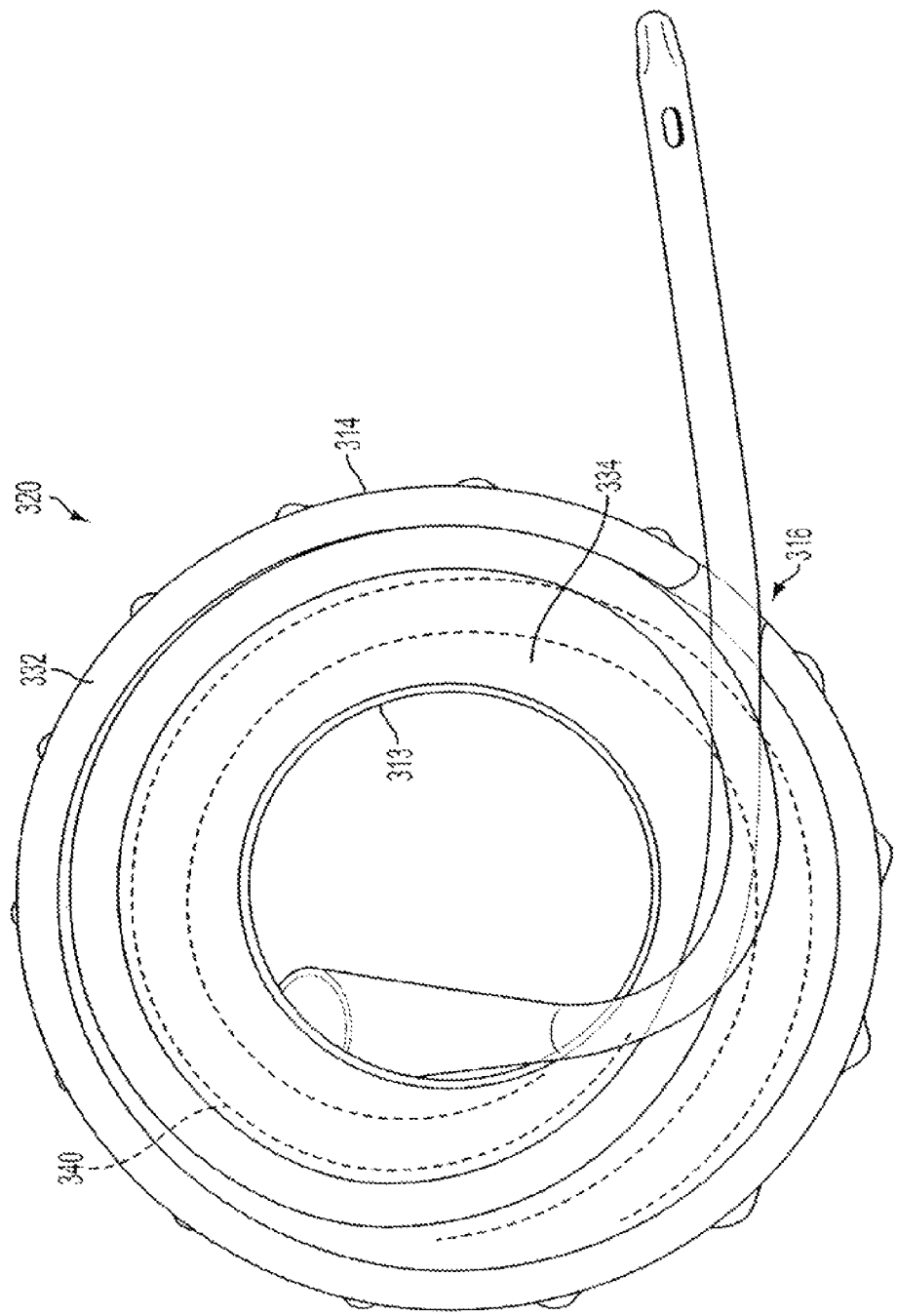
FIG. 3B shows a conceptual drawing of a top element of a catheter assembly.
Figure 3C:
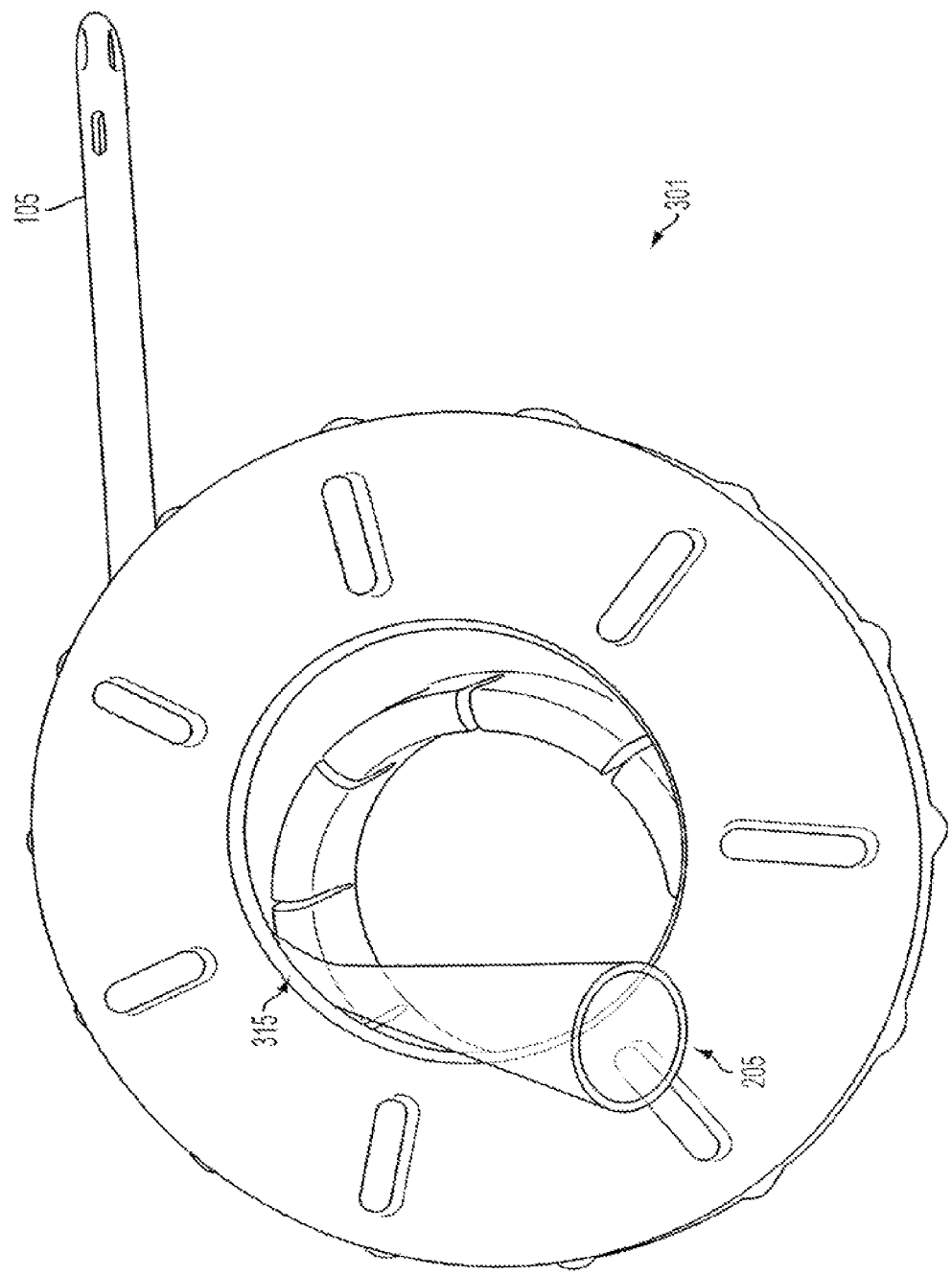
FIG. 3C shows a conceptual drawing of un assembled top and bottom elements of a catheter assembly.
Figure 3D:
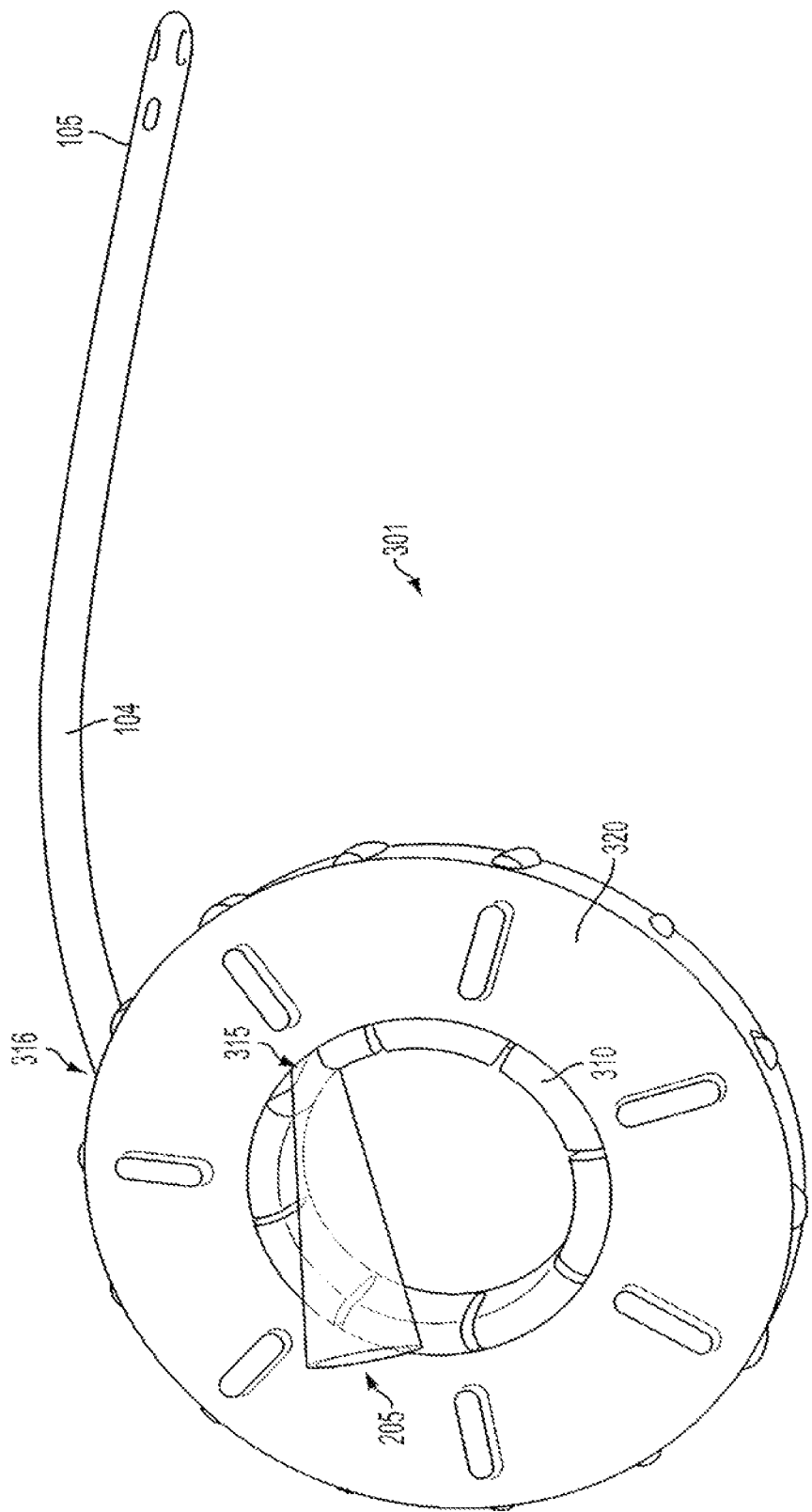
FIG. 3D shows a conceptual drawing of an assembled catheter assembly.
Figure 3E:
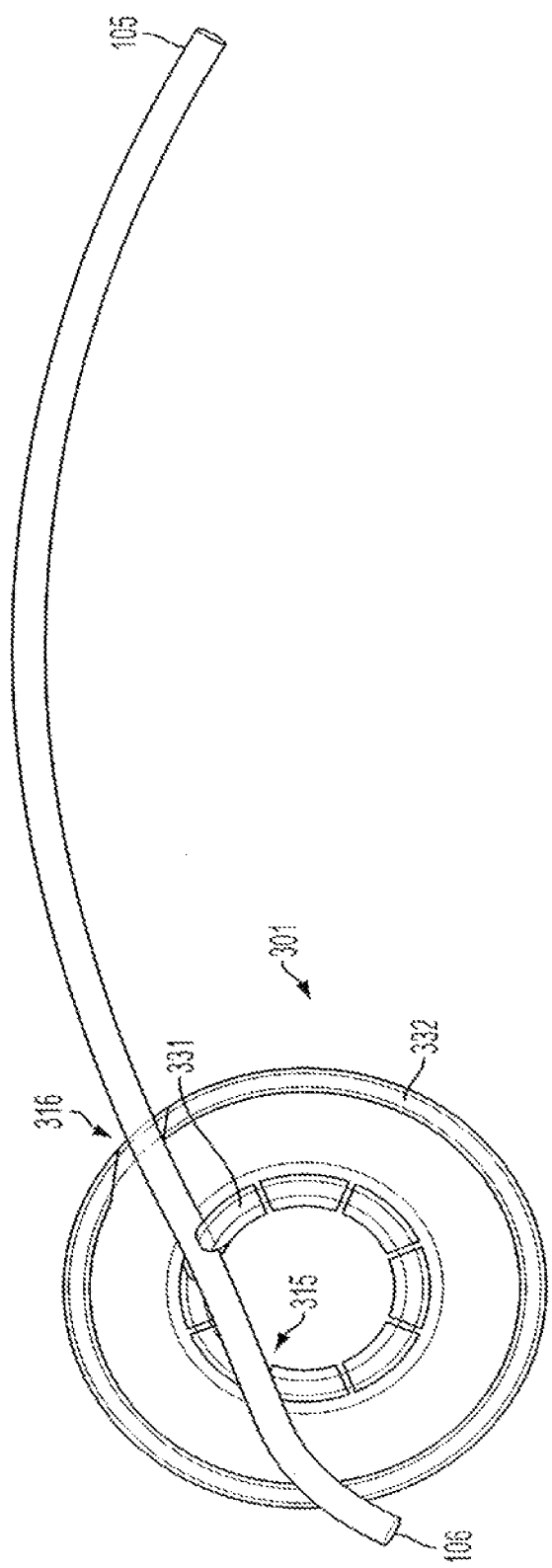
FIG. 3E s shows a conceptual drawing of a bottom element of a catheter assembly with a catheter attached thereto.

FIGS. 3A and 3B show conceptual drawings of a bottom element and a top element, respectively, of the catheter assembly FIGS. 3C and 3D show conceptual drawings of the bottom and top elements unassembled and assembled respectively, FIG. 3E shows a conceptual drawing of the catheter uncoiled and attached to the catheter assembly.

Catheter Assembly Elements.

As shown in FIGS. 3A and 3B, a catheter assembly 301 can include a bottom element 310 and a top element 320. The bottom element 310 can include an internal bottom edge 311 and an external bottom edge 312.

Similarly, the top element 320 can include an internal top edge 313 and an external top edge 314. In one embodiment, the internal bottom edge 311 is similarly sized as the internal top edge 313, and is disposed for coupling thereto. Similarly, in one embodiment, the external bottom edge 312 is similarly sized as the external top edge 314, and is disposed for coupling thereto.

In one embodiment, the internal bottom edge 311 and the internal top edge 313 are each substantially circular, and are disposed for rotation about a common axis, with the effect that rotation of the bottom element 310 with respect to the top element 320 allows the internal bottom edge 311 and the internal top edge 313 to move radially, with respect to each other, about that common axis.

Similarly, in such embodiments, the external bottom edge 312 and the external top edge 314 are each substantially circular, and are disposed for rotation about that same common axis, with the effect that rotation of the bottom element 310 with respect to the top element 320 allows the external bottom edge 312 and the external top edge 314 to move radially, with respect to each other, about that common axis.

After reading this application, those skilled in the art will recognize that the bottom element 310 and the top element 320 may move radially with respect to each other by any one of a number of alternatives, each of which would be workable, is within the scope and spirit of the invention, and would not require further invention or undo experiment. For example, the bottom element 310 may move while the top element 320 is relatively stationary, the bottom element 310 may be relatively stationary while the top element 320 may move, or both the bottom element 310 and the top element 320 may move.

In one embodiment, the internal edge 311 includes an internal hole 315, through which the proximal catheter end 106 can be placed. In those embodiments in which the proximal catheter end 106 is relatively wider than the main portion of the catheter 104, the proximal catheter end 106 has the effect of restricting the proximal catheter end 106 from slipping through the internal hole 315, and the effect of anchoring the proximal catheter end 106 at the internal edge 311 of the bottom element 310.

While this application describes an assembly in which the proximal catheter end 106 is flared, and that the flaring of the proximal catheter end 106 has the effect of restricting the proximal catheter end 106 from slipping through the internal hole 315, in the context of the invention, there is no particular requirement for any such limitation. The catheter 104 can be used to void urine, with the flared proximal catheter end 106 having other purposes, such as for aim or otherwise.

In one embodiment, the bottom element's internal edge 311 includes a flexible protruding wall, which can be coupled to the top element 320. In alternative embodiments, the top element's internal edge 313 includes the flexible protruding wall, which can be coupled to the bottom element 310. This has the effect that the bottom element 310 and the top element 320 form a spool-like shape, including a center around which the catheter 104 can be wound.

In one embodiment, the top element's external edge 313 includes a protruding wall, not necessarily coupled or flexible, which can be mated to the bottom element 310. In alternative embodiments, the bottom element's external edge 312 includes a protruding wall, not necessarily coupled or flexible, which can be mated to the top element 320. This has the effect that the bottom element 310 and the top element form a closed spool-like shape, including an external wall within which the catheter 104 can be wound.

Catheter Assembly Joinder.

As shown in FIGS. 3C and 3D (FIG. 3C showing an unattached assembly and FIG. 3D showing an attached assembly), in one embodiment, when the bottom element 310 and the top element 320 are coupled together, they form a donut-shaped space, having a centrally-located internal core wall 331, a peripherally-located external restraining wall 332, a bottom restraining wall 333, and a top restraining wall 334.

In one embodiment, the donut-shaped space is seen to have a substantially circular internal core wall 331, a substantially circular external restraining wall 332, a substantially flat bottom restraining wall 333, and a substantially flat top restraining wall 334. However, in the context of the invention, there is no particular requirement for any such limitation.

For a first example, the substantially circular internal core wall 331 and the substantially circular external restraining wall 332 might each be polygonal in shape, such as one or more of them forming a multi-sided regular polygon.

For a second example, the internal core wall 331 and the external restraining wall 332 might each define one or more additional holes, with the effect of not necessarily defining solid walls.

For a third example, one or more of the bottom restraining wall 333 and the top restraining wall 334 need not be substantially flat; instead one or more of them could define a bulge, an inverse bulge, or some other surface.

For a fourth example, one or more of the bottom restraining wall 333 and the top restraining wall 334 might each define one or more additional holes, with the effect of not necessarily defining solid walls.

The internal core wall 331 could be defined by the joinder of the bottom element's internal edge and the top element's internal edge. The external restraining wall 332 could be defined by a joinder of the bottom element's external edge and the top element's external edge. The bottom restraining wall 333 could be defined by that portion of the bottom element 310 from its internal bottom edge 311 to its external bottom edge 312. The top restraining wall 334 could be defined by that portion of the top element 320 from its internal top edge 313 to its external top edge 314.

After reading this application, those skilled in the art would see that there are other constructions, dispositions, and other alternative structures for the bottom element 310 and the top element 320, that such alternative structures would be workable without further invention or undue experiment, and are within the scope and spirit of the invention.

For a first example, the bottom element 310 could include portions of the structure described herein to be part of the top element 320, or vice versa. Such examples could involve including one or more portions of the internal core wall 331 in the bottom element 310, the top element 320, shared between the bottom element 310 and the top element 320, or otherwise assigned in parts among the bottom element 310 and the top element 320.

For a second example, the structures described herein could be divided otherwise than a bottom element 310 and a top element 320, or could include more than two such elements, or could include elements which are mated together at different locations or in different ways.

In one embodiment, the catheter 104 and the flexible tubing 201 are disposed within the donut-shaped space, in such manner as to form a substantially flat spiral, such as shown in FIG. 3D. However, in the context of the invention, there is no particular requirement for any such limitation.

For a first example, there is no particular requirement that the spiral is substantially flat.

For a second example, the catheter 104 might be disposed within the donut-shaped space in such manner as to form a helix or other coil 340, with the effect that the catheter 104 can be wound in parallel or more than once within the donut-shaped space.

In one embodiment, the catheter 104 is disposed with the distal tubing hole 203 being placed through the external hole 316, with the effect that the catheter 104 can be drawn out from the catheter assembly 301. This would have the effect that the catheter 104 would be uncoiled as it is drawn out from the catheter assembly 301, reducing the portion of the catheter 104 remaining within the catheter assembly 301.

In one embodiment, the catheter 104 is disposed with the proximal catheter end 106 being placed through the internal hole 315, with at least two effects. First, the proximal catheter end 106 is substantially anchored by its placement at the internal hole 315, with the effect that the catheter 104 is relatively resistant to being pulled completely out of the catheter assembly 301. Second, the proximal catheter end 106 is substantially available at a location external to the catheter assembly 301, with the effect that the catheter 104 can convey liquids from the distal catheter end 105 to the proximal catheter end 106, so that urine can be voided from the urethra into an appropriate receptacle, such as a public toilet, or alternatively into a urinary receiving bag or other medical equipment.

In one embodiment, the bottom element 310 and the top element 320 move radially with respect to each other when the catheter 104 is extended from the catheter assembly 301.

Similarly, the bottom element 310 and the top element 320 can be disposed to move radially in an opposite direction, with the effect that the catheter 104 is retracted into the catheter assembly 301, with one or more effects. For example, the catheter's distal end 105 can be retracted to a point where it is withdrawn inside the catheter assembly 301, and the catheter assembly 301 repackaged, such as for disposal.

In one embodiment, the bottom element 310, the top element 320, or both, can include bumps, handles, ridges, or other elements, suitable for the urinary catheter patient to easily move the bottom element 310 radially with respect to the top element 320.

For a first example, the bottom element 310, the top element 320, or both, can include radially disposed ridges, with the effect that the urinary catheter patient can move the bottom element 310 radially with respect to the top element 320 using their fingers and winding one or more of the bottom element 310 and the top element 320 about their common axis.

For a second example, the bottom element 310, the top element 320, or both, can include ridges disposed on at least a portion of the external restraining wall 332, with the effect that the urinary catheter patient can move the bottom element 300 and radially with respect to the top element 320 using their fingers and winding one or more of the bottom element 310 and the top element 320 about their common axis.

Catheter Attachment to Assembly.

As shown in FIG. 3E, the catheter 104 is coupled at the first point described with respect to FIGS. 3A and 3B and the second point described with respect to FIGS. 3C and 3D.

As described above, the catheter 104 is placed through the external hole 316, with the effect that the catheter 104 can be drawn out from the catheter assembly 301. In FIG. 3E, the catheter 104 is shown already drawn out from the catheter assembly 301, so as to form a relatively straight-line element, such as might occur during use.

As also described above, the catheter 104 is disposed with the proximal catheter end 106 being placed through the internal hole 315, with the proximal catheter end 106 being substantially anchored by its placement at the internal hole 315. In FIG. 3E, the catheter 104 is shown with the proximal catheter end 106 already substantially anchored by its placement at the internal hole 315, such as might occur during use.

After reading this application, those skilled in the art would recognize that this particular disposition of the assembly as described is not absolutely required, and that many variants thereof would be workable and would be within the scope and spirit of the invention, and would not require further invention or undue experiment.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular embodiments. Functionality may be separated or combined in procedures differently in various embodiments of the disclosure or described with different terminology. These and other variations, modifications, additions, and improvements may fall within the scope of the disclosure as defined in the claims that follow.

We claim:

1. A method of using a urinary catheter to at least partially void a bladder, the method comprising:
   opening a circular enclosure device housing the catheter;
   advancing a distal end of the catheter out of an opening in the enclosure device without directly touching the catheter;
   advancing the distal end of the catheter into a urethra by holding a sheath disposed over a portion of the catheter and without directly touching the catheter;
   sliding the sheath proximally along the catheter;
   advancing the distal end further into the urethra, holding the sheath but not directly touching the catheter; and
   at least partially voiding the bladder while a portion of the catheter remains in the enclosure device and while a proximal end of the catheter extends out of a central, unenclosed hole in the enclosure device, such that urine voided from the bladder passes through the catheter and out the proximal end.

2. A method as in claim 1, further comprising opening a sealed package containing the enclosure device and the catheter, before opening the enclosure device.

3. A method as in claim 1, wherein sliding the sheath proximally along the catheter lubricates a portion of the catheter with a lubricant.

4. A method as in claim 3, wherein the lubricant is stored within a portion of the enclosure device that houses the catheter and the sheath and is pre-applied to at least one of the catheter or the sheath, such that no additional step is required to apply the lubricant to the catheter.

5. A method as in claim 1, wherein advancing the distal end of the catheter out of the opening comprises turning a top portion of the enclosure device relative to a bottom portion of the enclosure device to unspool the catheter and thus advance the distal end out of the opening.

6. A method as in claim 5, further comprising, after at least partially voiding the bladder: removing the catheter from the urethra; turning the top portion of the enclosure device relative to the bottom portion to wind the catheter at least partially back into the enclosure device; and disposing of the catheter and the enclosure device.

7. A method as in claim 1, wherein advancing the distal end of the catheter into the urethra comprises: holding the sheath, which is tubular and concentrically disposed around a portion of the catheter and not attached to the enclosure device; and advancing the sheath toward the urethra to advance the catheter into the urethra.

8. A method as in claim 1, further comprising attaching a urine receiving bag to the proximal end of the catheter before voiding the bladder.

* * * * *